US00PP21053P3

(12) United States Plant Patent
Liu et al.

(10) Patent No.: US PP21,053 P3
(45) Date of Patent: Jun. 8, 2010

(54) MINT PLANT NAMED 'METOLIUS'

(50) Latin Name: *Mentha canadensis*
Varietal Denomination: Metolius

(75) Inventors: Jie Liu, Eugene, OR (US); Deven Holmgren, Eugene, OR (US); Mark Morris, Eugene, OR (US)

(73) Assignee: A. M. Todd, Eugene, OR (US)

( * ) Notice: Subject to any disclaimer, the term of this patent is extended or adjusted under 35 U.S.C. 154(b) by 115 days.

(21) Appl. No.: 12/081,071

(22) Filed: Apr. 10, 2008

(65) Prior Publication Data

US 2009/0260119 P1 Oct. 15, 2009

(51) Int. Cl.
*A01H 5/00* (2006.01)

(52) U.S. Cl. ..... Plt./259

(58) Field of Classification Search ..... Plt./259
See application file for complete search history.

*Primary Examiner*—Susan B McCormick Ewoldt
(74) *Attorney, Agent, or Firm*—Andreas Baltatzis; Kramer & Amado, P.C.

(57) ABSTRACT

A new and distinct variety of *Mentha canadensis* ('Metolius') is characterized by its unique oil chemistry and flavor profile resembling that of peppermint oil, and by its tolerance to *Verticillium* wilt (*Verticillium dahliae*) and mint rust (*Puccinia menthae*). DNA microsatellite marker analysis has shown that 'Metolius' is a distinct variety of *M. canadensis*.

2 Drawing Sheets

Latin name of the genus and species of the plant claimed: *Mentha canadensis*.

Variety determination: 'Metolius'.

FIELD OF THE INVENTION

The present invention relates to a new and distinct mint botanically known as *Mentha canadensis*. The new variety has been named 'Metolius' and will be referred as such hereafter.

BACKGROUND OF THE INVENTION

The present invention is a new variety of the mint species *Mentha canadensis* (common name American cornmint/Japanese peppermint). The essential oil industry refers to some members of the *Mentha canadensis* species as "*Mentha arvensis*." This includes such popular varieties as 'Shivalik,' 'Kosi,' and 'Kalka.' Botanically, however, these plants are *M. canadensis* species, with *Mentha arvensis* being a different and significantly less commercial mint species commonly referred to as a cornmint. The botanical differences allow one to differentiate between the two species through the use of current botanical keys for the genus *Mentha*. The use of "*Mentha arvensis*" by the industry should be interpreted as a colloquial industry usage for an "oil type" and not one of botanical specificity as these plants are correctly botanically identified as *M. canadensis*. For further information on mint species, see Lawrence, B. ed., 2007. *Mint: The Genus Mentha*. CRC Press, Boca Raton, Fla.; see also Tucker, A.O. and T. Debaggio, 2000. *The Big Book of Herbs*. Interweave Press, Inc., Loveland, Colo.

The new mint plant of the present invention was developed in an effort to cultivate a mint variety having a peppermint type oil and flavor profile, and greater tolerance to *Verticillium* wilt (*Verticillium dahliae*) and mint rust (*Puccinia menthae*) compared to that of commercial peppermint (*Mentha piperita*). Furthermore, 'Metolius' produces a peppermint-type oil that varies minimally in oil profile based on plant maturity.

The inventors explored ways of creating genetically distinct mint plants through somatic hybridization of unpatented varieties of *Mentha canadensis* and *Mentha piperita*. In 2002 'Metolius' was created using this method. Specifically, the parental stock that was used to create 'Metolius' consisted of unpatented germplasms of *Mentha×piperita* and *Mentha canadensis* species. The features of 'Metolius' are compared to the parent *Mentha canadensis*.

Since 2002, the plant has been under continuous evaluation at the Applicants' facilities in Eugene, Oreg. and Sunnyside, Wash., as well as under small-scale commercial programs located in Idaho, Washington, and Eastern Oregon. Asexual propagation through stem and rhizome cuttings have been successfully carried out many times in Eugene, Oreg. and Sunnyside, Wash. The resulting propagules have remained stable in appearance, oil quality, and other characteristics to the original plant.

SUMMARY OF THE INVENTION

The present invention relates to a new and distinct mint plant named 'Metolius' characterized by a unique oil chemistry and flavor profile resembling that of peppermint oil, and by its tolerance to *Verticillium* wilt (*Verticillium dahliae*) and mint rust (*Puccinia menthae*). Compared to 'Shivalik' and 'Kosi,' two commonly grown commercial varieties of *M. canadensis*, the plant is slightly shorter with darker green leaves when grown under similar growing conditions. The leaves are also slightly longer and narrower compared to 'Shivalik.' It matures about the same time as 'Shivalik' and 'Kosi.' The oil chemistry and flavor profile of 'Metolius' is also similar throughout its maturity when grown in Oregon, Washington, and Idaho.

BRIEF DESCRIPTION OF THE PHOTOGRAPHS

The accompanying color photographs of 'Metolius' show the new variety:

FIG. 1: shows the flower spike of 'Metolius'.

FIG. 2: shows the mature leaves of 'Metolius'.

DETAILED DESCRIPTION OF THE INVENTION

The present invention 'Metolius' is a new and distinct variety of a *Mentha canadensis* plant having the following characteristics that, in combination, are not exhibited in other *M. canadensis* plants:

l-Menthone to d-Isomenthone ratio of around 4.5%, typical of that found in commercial peppermint (*Mentha piperita*) oil. In other commercial *Mentha canadensis*, this ratio is around 2.0% or less.

l-Menthone of about 18% to 20%, compared to about 8% to 10% for other commercial *M. canadensis.* l-Menthol of about 62%, this compared to 42% and 72% for commercial peppermint and other commercial *M. canadensis* respectively.

l-Limonene of about 2.5% compared to 1.5% and under 2.0% for peppermint and other commercial *M. canadensis* respectively.

Oil having a clean peppermint-like flavor and odor profile.

When grown side by side with other commercial *M. canadensis*, 'Metolius' is a slightly shorter plant with leaves slightly darker, shorter, and narrower.

Botanical Description

*M. canadensis* 'Metolius' is an herbaceous perennial with an upright shrubby growth habit. The plant physically spreads by stolons, and it is reasonable for a single rooted cutting to spread and cover 3–4 square feet after one growing season. Numerous branching stems are produced each year with an eventual height of 70–80 cm. Compared to 'Shivalik' (not patented) and 'Kosi' (U.S. Plant Pat. No. PP12,426), two commonly grown commercial cornmints, the plant is slightly shorter with darker green leaves when grown under similar growing conditions. The leaves are also slightly longer and narrower compared to 'Shivalik.' It matures about the same time as 'Shivalik' and 'Kosi.'

'Metolius' has been grown in different field locations. It has also been grown under greenhouse conditions. Asexual propagation through stem and rhizome cuttings have been successfully carried out many times since 2002 at the Applicants' facilities in Eugene, Oreg. and Sunnyside, Wash. The resulting propagules have remained stable in appearance, oil quality, and other characteristics to the original plant. The basic morphological characteristics have remained consistent, with any minor differences easily attributed to differences such as climate, soils, fertilizer, or water regime. The distinguishing traits present in 'Metolius' remain constant in the asexually reproduced plants.

Oil Composition and Flavor

Although 'Metolius' has the same chemical components as other *M. canadensis* varieties, the relative amount of several components resembles the distribution typically found with peppermint oil. The l-Menthone / d-Isomenthone ratio of about 4.5 for 'Metolius' is typical of a standard *Mentha piperita* which contributes to the clean peppermint-like flavor characteristics noted with this oil. The level of l-Menthone is about 18.0% for both 'Metolius' and commercial peppermint compared to 10% for other commercial *M. canadensis* varieties. The level of l-Menthol is about 62%, for 'Metolius' compared with 42% and 72% for peppermint and other commercial *M. canadensis*, respectively. The l-limonene level for 'Metolius' is about 2.5% compared to 1.5% and less than 2.0% for peppermint and other commercial *M. canadensis* respectively.

Stem and Leaves:

'Metolius' has a square stem and therefore does not have a stem diameter. The stem dimensions measure 8–9 mm long per side of the square for a total dimension of 8–9 mm by 8–9 mm when mature. Measurements were taken near the base of the stem, since this measurement will decrease towards the tip of the plant. The plant matures to approximately 70–80 cm in length. Internode length varies considerably along the stem from less than 20 mm near the base and at the apex, increasing to an average of 50 mm along the midstem. Under crowded conditions, internode length can even be higher, up to 80 mm. As a mint plant, 'Metolius' spreads by underground stolons and the number of stems is highly variable. Stems and ovate leaves are pubescent, oppositely arranged on the stem with an equilateral base, an acute apex, serrate margin and decreasing in size towards the apex of a blooming stem. The average mature leaf length is 60 mm. Average leaf width is 30 mm. Venation pattern is pinnate. Dorsal leaf surface color is medium yellow green (147A — Yellow-Green Group), with a lighter ventral color (147B — Yellow-Green Group). Vein color is light yellow green (147C — Yellow Green Group). The mature petiole length is 6–8 mm. Petiole width is 3–4 mm. Petiole thickness is 1–2 mm. Petiole color is light yellow green (147C — Yellow-Green Group). Stem color is also light yellow green (146C — Yellow-Green Group). Color numbers are from The R.H.S. Colour Chart (Royal Horticultural Society (Great Britain), London 1966). The base of the stem has a more "woody" appearance and quality with more brownish coloring and fissures. The fragrance is a clean peppermint-like aroma.

Flower:

Like other *Mentha canadensis* species, 'Metolius' possesses a flower spike with a pair of bract-like leaves subtending each verticillaster. The individual flowers contain a 4-lobed, nearly regular, mostly white, tubular corolla with a slight light purple coloration near the base (85C — Violet Group). The flower is 8 mm long from the base of the calyx to the tip of the forked white stigma. The calyx generally has five teeth fused at the base forming a short tube and is 3 mm long. The calyx, peduncle and pedicel colors are light yellow green (147C — Yellow-Green Group). Each flower has one pistil with an 8 mm long white style and four epipetalous stamens that are exerted with 4 mm long white filaments. The white anthers are less than 1 mm. Pollen is not produced in abundance. That which is produced has a pale yellow color. The formation of seed is a rare event. There is no obvious flower fragrance.

The above description is based on observations of a field plot made during the middle of the second growing season of the field plot outdoors in western Oregon.

Genetic Analysis

In order to determine the precise genetic identity of 'Metolius', DNA (SSR) microsatellite marker analysis was conducted using known methods as described by T. A. Holton, *Plant genotyping by analysis of microsatellites* 15–28, in *Plant Genotyping: The DNA fingerprinting of plants* (R.H. Henry ed., 2001). Comparing microsatellite DNA (SSR) methodologies with other DNA genotyping techniques such as RFLPs, AFLPs, and RAPDs, has established that microsatellite DNA (SSR) offers a more reliable, repeatable method for characterization with an increased ability to differentiate among plant varieties. The technique has been widely used in animal, plant, and human identification and population studies. The drawback of the technique is the initial high cost of developing the markers. However, once these markers have been developed, they can be simply used by combining PCR with GenScan technologies.

During 2003–2005 period, a project was conducted using 34 microsatellite markers to genetically identify 'Metolius.' A total of 4 different populations of *M. canadensis* were collected. Their microsatellite DNA profiles were then compared against a total of 8 recognized peppermint varieties along with other closely related *Mentha* species including spearmint (*M. spicata*).

A total of 179 microsatellite characters/profiles were found from the 34 markers. Genetic distances as measured by total character differences among different populations of the same variety ranged from 0–14. The values among recognized peppermint varieties ranged from 16–42. The values between 'Metolius' populations and other *M. canadensis* populations ranged from 0–4. A phylogenetic analysis was conducted as well as a principal component analysis. Both revealed that 'Metolius' and *M. canadensis* populations clustered together and formed a strongly supported *M. canadensis* species group. Based on these genetic analyses, 'Metolius' was classified as a variety of *M. canadensis*. The differences observed among the *M. canadensis* samples are typical of the differences noted among different varieties of the same species, and allow the identification of 'Metolius' from other varieties of *M. canadensis*.

Plant Disease Resistance/Susceptibility

Observations of 'Metolius' since 2002 indicate that rust does not infect 'Metolius' under any observed circumstances. Furthermore, 'Metolius' has exhibited high tolerance to *Verticillum* wilt through the same observation period.

Winter Hardiness and Drought/Heat Tolerance

'Metolius' is winter hardy and heat tolerant in the common mint growing regions of the world. No specific claims are made to exceptional cold hardiness or heat tolerance.

What is claimed is:

1. A new and distinct *Mentha canadensis* plant named 'Metolius' substantially as herein described and illustrated.

* * * * *

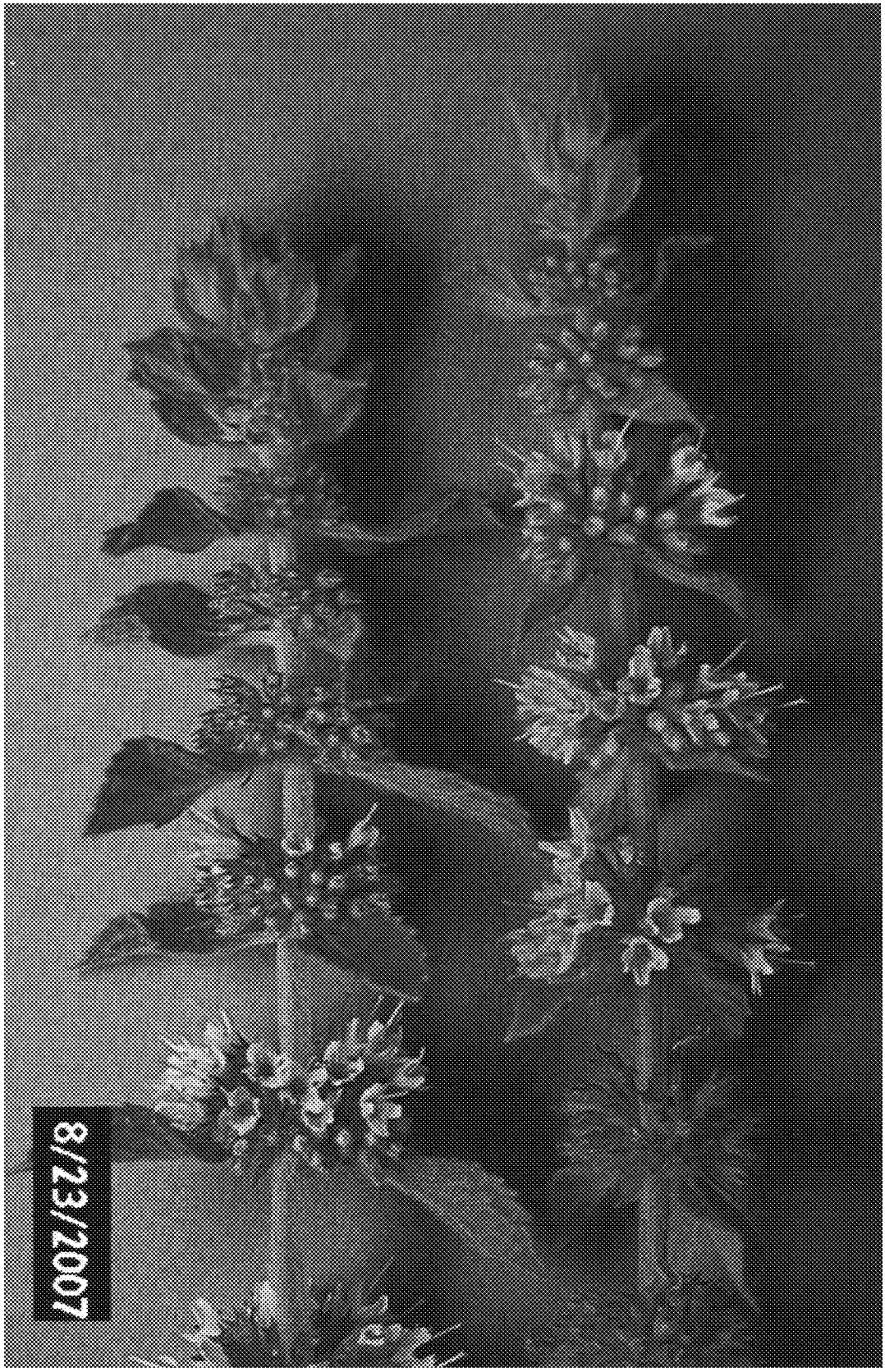
8/23/2007

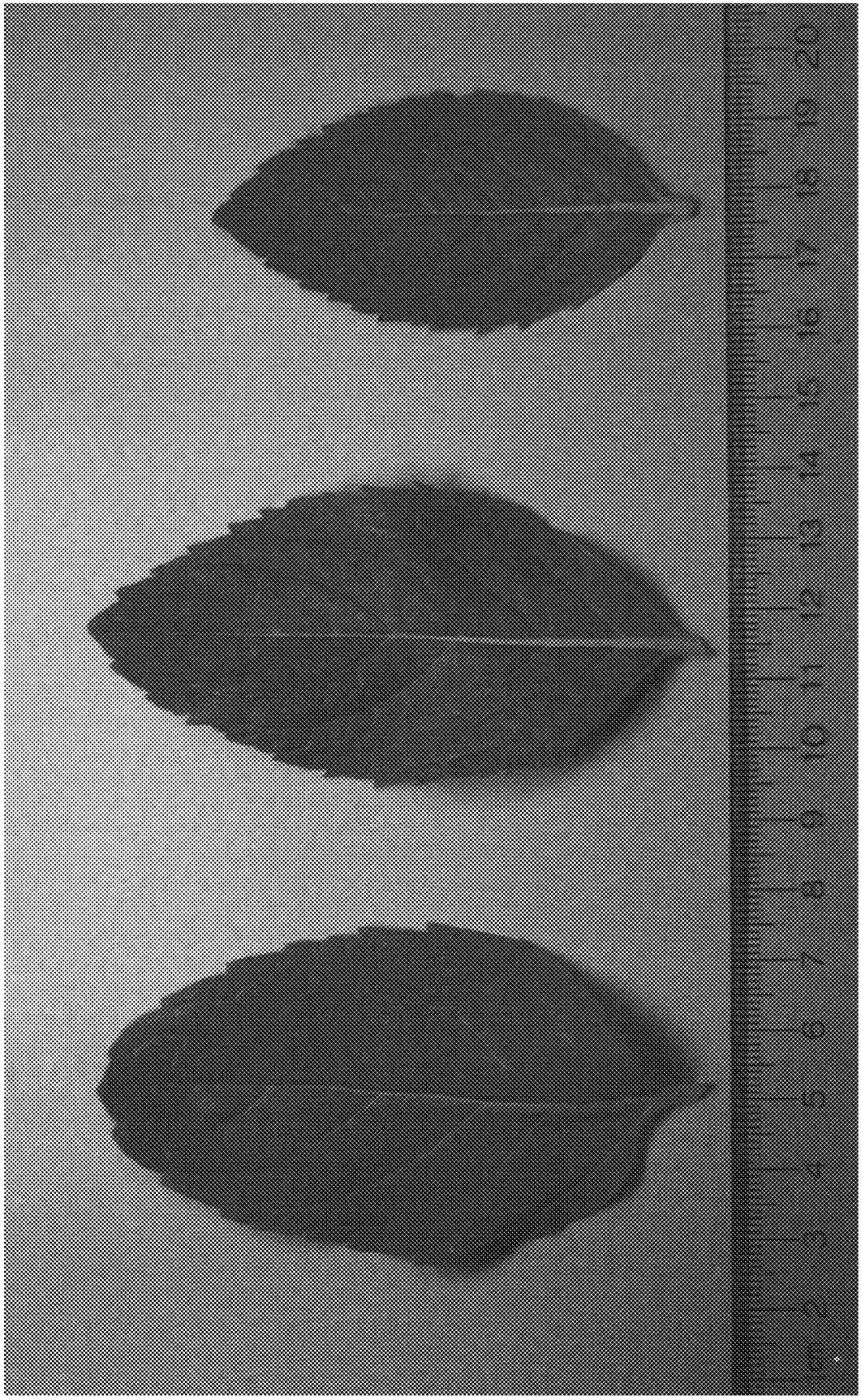
1
2
3
4
5
6
7
8
9
10
11
12
13
14
15
16
17
18
19
20